United States Patent [19]

Underwood et al.

[11] Patent Number: 4,876,108
[45] Date of Patent: Oct. 24, 1989

[54] METHOD OF USING FAST PYROLYSIS LIQUIDS AS LIQUID SMOKE

[75] Inventors: Gary Underwood, Manitowoc, Wis.; Robert G. Graham, Nepean, Canada

[73] Assignee: Ensyn Engineering Associates Inc., Ontario, Canada

[21] Appl. No.: 119,673

[22] Filed: Nov. 12, 1987

[51] Int. Cl.$^4$ ............................................. A23L 1/221
[52] U.S. Cl. ................................... 426/650; 426/315; 426/431; 426/520; 426/524; 426/655
[58] Field of Search ............... 426/655, 650, 314, 520, 426/524, 431, 315; 201/2.5

[56] References Cited

U.S. PATENT DOCUMENTS

| | | | |
|---|---|---|---|
| 3,106,473 | 12/1961 | Hollenbeck | 426/650 |
| 4,359,481 | 11/1982 | Smits | 426/650 |
| 4,431,032 | 2/1984 | Nicholson | 426/315 |

FOREIGN PATENT DOCUMENTS

| | | |
|---|---|---|
| 932686 | 8/1973 | Canada . |
| 1121650 | 4/1982 | Canada . |
| 1193131 | 9/1985 | Canada . |
| 0246847 | 11/1987 | European Pat. Off. . |
| 1137637 | 12/1968 | United Kingdom . |

OTHER PUBLICATIONS

"The Pyrolysis Under Vacuum of Aspen Poplar", by Christian Roy et al., (1985), *Fundamentals of Thermochemical Biomass Conversion*, pp. 237–256.

"Production of Liquids from Biomass by Continuous Fast Pyrolysis", *Bioenergy 84* vol. 3, *Biomass Conversion*, D. S. Scott and J. Piskorz, pp. 15–22.

"Fast Pyrolysis of Biomass", by R. G. Graham & M. Bergougnou, Journal of Analytical and Applied Pyrolysis 6 (1984), pp. 95–135.

"On the Mechanism of the Rapid Pyrolysis of Cellulose", J. Piskorz et al.

"Cacterisation des Jus Pyrolytiques en Provenance de Differents Procedes de Conversion du Bois", H. Menard et al., Fifth Canadian Bioenergy R and D. Seminar (84).

"Rapid Mixing Studies Between Transported Solids in an Ulta-Rapid Fluidized Reactor", D. A. Berg et al.; Presented at Powder and Bulk Solids Conference, Rosemount, Ill., (May 1985).

"Characterization of Solids Mixing in an Ultra-Rapid Fluidized Reactor", D. A. Berg et al., Presented at Powder and Bulk Solids Conference, Rosemount, Ill., (May 12-15, 1986).

*Primary Examiner*—R. B. Penland
*Attorney, Agent, or Firm*—Marhsall, O'Toole, Gerstein, Murray & Bicknell

[57] ABSTRACT

An aqueous wood smoke solution for flavoring foodstuffs is produced by heating in an oxygen starved atmosphere ground wood or cellulose to between 400° C. and 650° C. within 1.0 second; maintaining the said wood or cellulose and the primary pyrolysis vapors between 400° C. and 650° C. for between 0.03 and 2.0 seconds; reducing the temperature of the pyrolysis products to below 350° C. within 0.6 seconds; separating and collecting the water soluble liquid products; and diluting the said water soluble liquid products with water to achieve a partial phase separation and to reduce the benzo(a)pyrene concentration to less than 1.0 ppb.

17 Claims, 4 Drawing Sheets

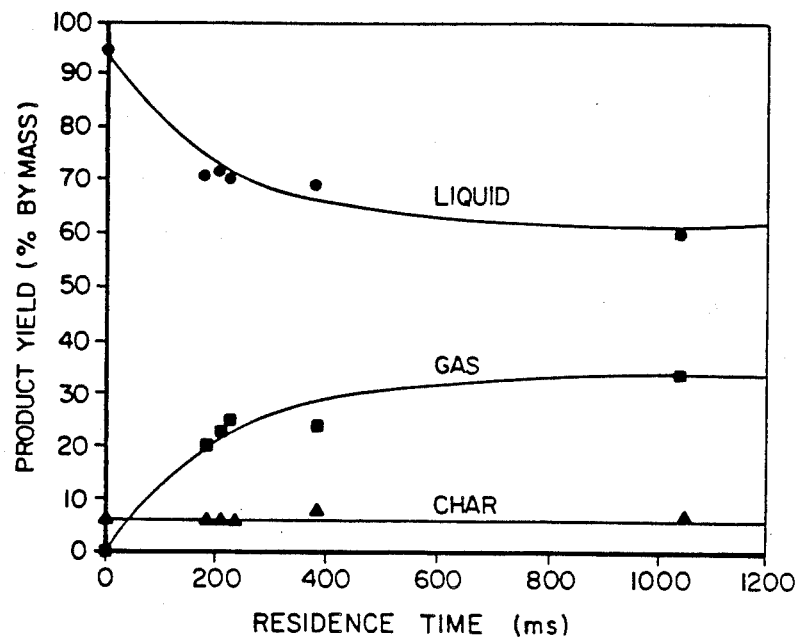
FIG. 4  FAST PYROLYSIS (650°C): PRODUCT YIELD VS RESIDENCE TIME
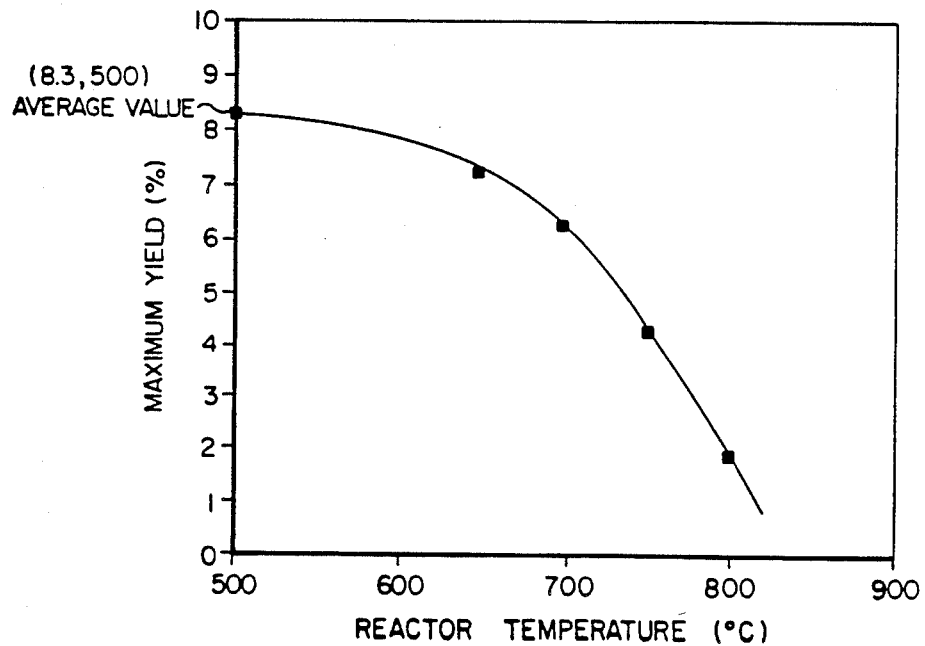
FIG. 5  FAST PYROLYSIS OF WOOD. MAXIMUM HYDROXYACETALDEHYDE YIELD VS TEMPERATURE

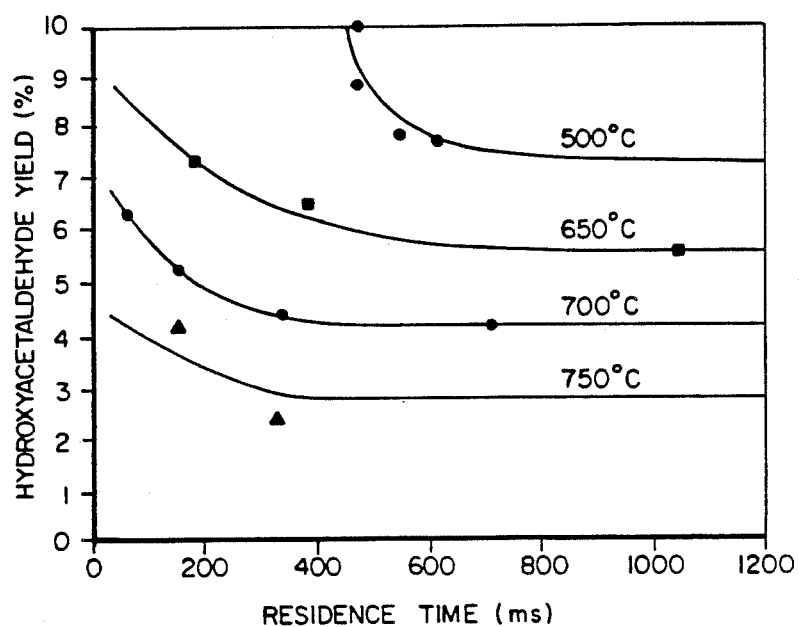
FIG. 6  FAST PYROLYSIS OF WOOD. HYDROXACETALDEHYDE VS RESIDENCE TIME

METHOD OF USING FAST PYROLYSIS LIQUIDS AS LIQUID SMOKE

This invention generally relates to the use of liquid smoke manufactured by a fast pyrolysis method for processing, flavoring and coloring, meat, fish, poultry and other food products.

BACKGROUND OF THE INVENTION

Use of liquid smoke solutions as a replacement for smoking by direct contact with smoke produced from wood has become a standard industry practice. When applied to the surface of meats and other proteinaceous foodstuffs, liquid smoke will not only give the item a characteristic smoke flavor, but will react with the proteins to produce the dark color typical of smoked foods.

One such liquid smoke preparation used commercially, for surface applications is the aqueous smoke flavoring described in Hollenbeck U.S. Pat. No. 3,106,473. This product is produced by partial combustion of hardwood sawdust with limited access to air, followed by subsequent solvation of the desirable smoke constituents into water. A heavy, water insoluble phase which contains tar, polymers, polycyclic aromatic hydrocarbons including benzo[a]pyrene, waxes and other undesirable products unsuitable for use in food applications is discarded.

Smoke is a complex and variable mixture of chemicals which are produced from pyrolysis reactions and includes vaporous compounds which are normally liquid at room temperature. Pyrolysis is a general term for the thermal decomposition of any organic material (i.e. wood, plants, fossil fuels etc.) and can occur during a combustion process or in the absence of combustion. In the former, the oxidation or burning of a portion of the organic matter provides the heat required to vaporize and decompose the remainder. In the absence of combustion, heat must be supplied indirectly from some other source (i.e. radiation, a solid or gaseous heat carrier, or conduction through reactor walls, etc.).

Pyrolysis produces liquids (i.e. condensable vapors), gases (non-condensables) and solids (char and ash) in varying proportions depending upon reaction conditions. The liquids can be further sub-divided into water soluble organics and non-water soluble tars. It is known that the desirable active ingredients for smoke flavoring are among the water soluble condensable vapors (liquids).

Currently liquid smoke is made using conventional pyrolysis which is characterized by relatively slow thermal reactions occurring at moderate temperatures. In the commercial processes, the wood feedstock is dried and ground to sawdust and fed to a reactor system. A typical average reactor temperature is approximately 420° C. Depending on the method of heating, the temperature gradient in the reactor may be from 600° C. at the heater to 250° C. at the bulk wood surface. Residence times of solids (wood/char) and vapors are approximately 10 minutes and 1 minute respectively.

Conventional pyrolysis produces liquid, gas and char yields which are typically 35, 35 and 30% by mass of the wood feedstock, respectively. Since the water insoluble constituents are between 50 and 65% of the total liquids derived from the wood content, the net yield of raw liquid smoke is relatively low (i.e. 12 to 20% of the wood feedstock).

The pyrolysis products are often passed through a water bath or scrubber. The gaseous products pass through the water bath. The solids and water insoluble tars precipitate out of the water with the water soluble organics are collected in the water as liquid smoke.

While there are hundreds of distinct chemical species present in liquid smoke, liquid smoke products have been characterized by three classes of chemicals according to distinct functional groups. The three classes are (1) acids, (2) carbonyls and (3) phenols This functional definition is useful since phenols are the primary flavoring compounds while carbonyls are responsible mainly for coloration and acids serve as a preservative. Acids and carbonyls also make a secondary contribution to flavor and they enhance the surface characteristics of the meat products.

Acids are measured as titratable acidity calculated as acetic acid. Phenols are calculated as 2,6-dimethoxyphenol. The procedure for determining phenols is a modified Gibbs method. Carbonyls are calculated as 2-butanone. The procedure for determining carbonyls is a modified Lappan-Clark method. The procedures for determining carbonyls and phenols are described in U.S. Pat. No. 4,431,032 the contents of which are incorporated herein by reference.

A further measurement that is used to characterize liquid smoke is the browning index. The browning index is used in the smoke flavoring industry to measure the browning performance of a liquid. The browning index is a colormetric technique that measures the extent to which the carbonyls react with glycine. The browning index is determined from the difference between the adsorption at 400 nanometers of the glycine reacted solution and a control sample.

The application of liquid smoke solutions to meat and other food products can be carried out in a number of ways. Where the characteristic smoked color is desired, spraying or dipping can be done on individual items in a batch or continuous mode. Where large batches are to be processed an atomized cloud of liquid smoke can be employed. Alternatively, sausages and hams may be processed in casings into which liquid smoke solutions have been incorporated. In any case, where surface color is the primary effect which is sought, a measure of total carbonyls is used to judge the quantity of smoke required. These compounds react with the available amino groups of proteins at the surface to form the smoked color. The concentration of a specific carbonyl, hydroxyacetaldehyde, is also a good indicator of the color forming potential of liquid smoke.

Prior methods of producing liquid smoke suffer from relatively low yields of desirable products and relatively high yields of the undesirable by-products. In addition the levels of benzo[a]pyrene, a known carcinogen, is relatively high, requiring subsequent dilution of the collected condensable vapors with water to separate out these compounds.

The requirement to dilute the collected condensables to limit the level of benzo[a]pyrene below 0.5 ppb prevents the production of liquid smoke having a total acid content above 13% or a browning index above 13.0 without subsequent concentration.

Recently new methods have been developed for the rapid thermal processing of carbonaceous feedstocks. These methods have been called fast or flash pyrolysis.

Fast or flash pyrolysis of wood or cellulose is a method of imparting a high heating rate to the wood for a very short time and then rapidly quenching the pyrolysis products to a temperature below 350° C. The heating rate for fast pyrolysis is greater than 1000° C. per second and vapor residence times are below 2.0 second. While fast pyrolysis methods are known, the research and development in this area has concentrated on producing liquid and gaseous fuels, and on optimizing the production of high energy value fuels.

One object of this invention is to provide a method of using the water soluble products from fast pyrolysis to produce liquid smoke in place of conventional liquid smoke to achieve greater yields and higher concentrations of desirable product and lower yields of gaseous and solid by-products, resulting in greater efficiency and resulting cost savings.

Specifically fast or flash pyrolysis results in higher hydroxyacetaldehyde and other carbonyl yields and lower char, benzo[a]pyrene and gas yields. The higher carbonyl yields effects a higher browning index.

Further cost efficiencies results from a faster rate of the reaction in fast or flash pyrolysis which permits greater processing efficiencies in that smaller reactor volumes are required to process a given quantity of feedstock.

Another object of this invention is to provide a method for preparing a smoke colored and smoke flavored food product by treatment of the said food products with the aforementioned liquid smoke solution.

Other objects and advantages of the invention will become apparent from the ensuing disclosure and claims.

SUMMARY OF THE INVENTION

Accordingly, the invention herein comprises a method of manufacturing and optimizing the liquid pyrolysis products from a fast or flash pyrolysis method to produce a liquid that is very suitable for use as liquid smoke. The liquid smoke of the invention herein is achieved in high yields, i.e. with low char and tar formation. It contains less than 1.0 ppb of benzo[a]pyrene, and preferably less than 0.5 ppb of benso[a]pyrene, a known carcinogen, and a higher coloring ability than liquid smoke produced by traditional methods.

Furthermore, these solutions will impart the desired smoked color to meat with milder, less smoky flavor than would be expected from slow pyrolysis liquid smoke solutions. The high ratio of carbonyls (the reactive color forming compounds) to phenols (the flavoring compounds) is indicative of this relatively high coloring ability, low flavor nature of fast pyrolysis liquid smoke solutions.

In accordance with the present invention there is provided a process of making an aqueous wood smoke flavoured solution for use in foodstuffs comprising:

(1) heating in an oxygen starved atmosphere ground wood or cellulose to between 400° C. and 650° C. within 1.0 second;

(2) maintaining the said wood or cellulose and the primary pyrolysis vapors between 400° C. and 650° C. for between 0.03 and 2.0 seconds and preferably between 0.03 and 0.60 seconds.

(3) reducing the temperature of the pyrolysis products to below 350° C. within 0.6 seconds;

(4) separating and collecting the water soluble liquid products;

(5) diluting the said water soluble liquid products with water to achieve a partial phase separation and to reduce the benzo[a]pyrene concentration to less than 1.0 ppb and preferably to less than 0.5 ppb.

In accordance with a further aspect of this invention there is provided a process of flavoring and coloring an edible food by contacting the food with an aqueous wood smoke flavored solution produced by fast or flash pyrolysis.

In accordance with another aspect of the present invention there is provided a process of producing a liquid smoke solution comprising:

(1) collecting the liquid condensate product obtained by fast or flash pyrolysis of ground wood or cellulose in an oxygen starved atmosphere, without the addition of water;

(2) combining one part of the pyrolysis liquid condensate with 0.25 to 25 parts by weight of water and then separating the resulting non-adqueous phase from the aqueous phase constituting the desired liquid smoke solution.

In accordance with yet another aspect there is provided a process in which sufficient water is added to produce a liquid smoke solution wherein the ratio of the browning index to the phenol concentration is greater than 8.9 to 1% carbonyls.

Since fast or flash pyrolysis liquids are produced without the addition of water, unlike conventionally produced liquid smoke solutions, they consist of a single phase. Due to the extremely fast heating rate and short residence time, these solutions are inherently low in benzo[a]pyrene content however the levels, while at least an order of magnitude less than the levels produced by conventional liquid smoke, are still too high for consumption in many countries. Therefore, to reduce the benzo[a]pyrene to less than 0.5 ppb, an addition of water to cause a separation of phases is necessary. Accordingly, the invention comprises the comestible, aqueous soluble fraction of fast pyrolysis products.

The use of this particular liquid in the liquid smoke flavoring industry results in a much improved liquid smoke that avoids a number of the shortcomings of the prior art, while at the same time, resulting in increased yields and a better quality product.

Using fast or flash pyrolysis methods, up to 80% yield of liquid products can be realized. Given the right operating parameters, the char yields will be around 6% with the remaining portion of the products being gaseous in nature. The char yields can be reduced to below 1% if desired.

Liquid smoke manufactured by fast pyrolysis methods exhibits increased total carbonyls, phenols and acids, and has a much improved browning index.

The total water soluble carbonyls, phenols, acids and browning index of a representative sample of commercial liquid smoke and products from two fast pyrolysis methods are set out in Table 1 below.

TABLE 1

ANALYSIS OF WATER SOLUBLE LIQUIDS
Yields From Wood

| Sample Source | Total Carbonyls (% w/w) | Total Phenols (% w/w) | Total Acids (% w/w) | Browning Index Units/ 100 g bone dry wood |
|---|---|---|---|---|
| 1. Fluidized Bed (500° C. 0.5 s) | 22.2 | 1.6 | 6.9 | 2877 |
| 2. Rapid | 20.7–26.0 | 1.3–2.0 | 6.2–7.3 | 2390–3400 |

TABLE 1-continued

ANALYSIS OF WATER SOLUBLE LIQUIDS
Yields From Wood

| Sample Source | Total Carbonyls (% w/w) | Total Phenols (% w/w) | Total Acids (% w/w) | Browning Index Units/ 100 g bone dry wood |
|---|---|---|---|---|
| Thermal Processing (600° C., 0.2 s) | | | | |
| 3. Commercial Liquid Smoke | 6.0 | 0.7 | 5.3 | 518 |

% w/w - % by weight of product yield from bone dry wood feedstock as measured in water soluble fraction As can be noted from Table 1, the yield of carbonyls is approximately 3 times better using liquids manufactured by a fast pyrolysis method over commercial liquid smoke, while the yield of phenols has more than doubled; the yield of acids has been improved, and the browning index is about 6 times better.

The level of benzo(a)pyrene, in the fast pyrolysis liquids before dilution and phase separation is at least an order of magnitude lower than liquids produced by known commercial process. This lower level of benzo(a)pyrene allows a more concentrated product to be produced. The total condensate from conventional pyrolysis contains approximately 750 ppb of benzo(a)pyrene.

The level of benzo(a)pyrene in the total condensate from fast pyrolysis is between 5 and 50 ppb.

With fast pyrolysis, after dilution and phase separation, the ratio of carbonyls to phenols is higher which is indicative of the high browning potential relative to the amount of flavor. In addition, the undesirable by-product yields of gas and solid char are lower and the corresponding disposal costs are lower.

Unconcentrated commercial liquid smoke has a browning index between 3.0 to 13. While methods are available for concentrating liquid smoke to achieve a browning index of up to 25, unconcentrated liquid smoke has a practical upper limit of about 13 as the benzo(a)pyrene levels become excessive if the liquid smoke is permitted to continue to concentrate above this level in the water collection baths.

Through the use of fast pyrolysis methods browning indexes of up to 45 can be achieved without using any concentration steps and with levels of benzo(a)pyrenes below 0.5 ppb.

The presence of hydroxyacetaldehyde is useful as an index to rate the value of the liquid for smoke coloring applications. The yield of this compound by fast or flash pyrolysis methods increases with a decrease in temperature from 900° to about 500° C. and a decrease in residence time. Yields of hydroxyacetaldehyde in excess of 8% by mass can be obtained at reaction temperatures of 550° or 600° C. and 100 millisecond vapor residence time.

The yield of hydroxyacetaldehyde is much greater from fast pyrolysis methods. A comprison of yields of hydroxyacetaldehyde from two fast pyrolysis methods and commercial liquid smoke is set out in Table 2. As can be noted, yields up to about 4 times higher are achieved using fast pyrolysis. Hydroxyacetaldehyde is one of the predominant carbonyls in wood pyrolysis liquids and is therefore used as an index to assess a liquid's potential for liquid smoke applications.

TABLE 2

CHEMICAL ANALYSIS OF THE PYROLYSIS LIQUIDS
(Hydroxyacetaldehyde Yields)

| Sample Source | Hydroxyacetaldehyde Yield (% w/w) |
|---|---|
| 1. Fluidized Bed (450 to 550° C., 0.5 s) | 7.5 to 8.5 |
| 2. Rapid Thermal Processing (550 to 700° C., 0.2 s) | 7.0 to 8.0 |
| 3. Commercial Liquid Smoke | less than 2% |

Hydroxyacetaldehyde (glycoaldehyde) and acetol (1-Hydroxy-2-Propanone) are the two predominant carbonyls in pyrolysis liquids. Hydroxyacetaldehyde is much more reactive in terms of browning and its presence is an excellent indication of the browning ability of the liquid. Acetol is a poor browner. The ratio of hydroxyacetaldehyde to acetol can therefore be used as an index of the effectiveness of the carbonyls in the liquids with respect to browning ability.

Analyses show that the ratio of hydroxy acetaldehyde to acetol in conventional liquid smoke is typically less than 1.0. However, the average ratio (4 samples) of hydroxyacetaldehyde/acetol in fast pyrolysis liquids is about 6 (5.9) while the maximum measured ratio is 7.2. In effect, not only are more carbonyls produced during fast pyrolysis (i.e. higher yields), but the carbonyls that are produced are more effective browning agents.

The parameters that should be optimized in any fast pyrolysis method to produce a suitable liquid product for use as liquid smoke, include:

(1) high heating rates of the wood feedstock (greater than 1,000° C. per sec.);

(2) a vapor residence time (i.e. the average time that the gas/vapor phase remains in the reactor) greater than 0.15 sec. and less than 1.0 sec. and preferably less than 0.6 sec.;

(3) isothermal reaction reactor temperatures between 400° and 800° C.; and (4) quenching of the liquid/vapor product to a temperature of less than 300° C. in less than 0.6 sec. in order to preserve the high liquid yields.

When vacuum pyrolysis apparatus is used, the heating rate of the wood or cellulose is much slower than with rapid thermal processing apparatus or with a fluidized bed reactor. Secondary pyrolysis reactions however are reduced by quickly removing and cooling the primary pyrolysis vapours. As such, the fast heating rate is not essential as long as the secondary reactions are limited.

The major components of the fast pyrolysis process are designed to achieve a very high temperature within a minimum amount of time as well as having a relatively short residence time at that temperature to effect pyrolysis of the wood or cellulose. This short residence time at high temperature has been achieved by a number of systems. One method is a vacuum pyrolysis process that is based on the principle that primary products can be withdrawn from the reactor under vacuum conditions before they have a chance to react further and produce secondary pyrolysis products. This method has been described in *Fundamentals of Thermo-Chemical Biomass*

Conversion R. P. Overend et al. (editors) Elsevier publishers, (1985) in an article entitled "Pyrolysis under Vacuum of Aspen Poplar" by Christian Roy, Bruno de Caumia, Dominique Brouillard and Hughes Menard, the contents of which are incorporated herein by reference. The solid wood feedstock remains in the reactor until completely reacted. Total liquid yields of between 68 and 74% by mass of the total wood feedstock have been reported at reaction temperatures of 450° C. and a solid heating rate of 10° C./min. and a residence time of up to 2 seconds. At a vapor residence time of about 2.0 seconds the char yields were between 16 and 20% by mass of the wood feed material.

A second method for obtaining fast pyrolysis is "flash" pyrolysis, using a fluidized bed reactor system operating at temperatures between 400° and 650° C. Total liquid yields of between 60 and 70% of the wood feed stock have been obtained with an average vapor residence time of 0.5 sec. The char yield was typically between 10 and 20% of the wood mass. Residence times of up to 3.0 seconds can be achieved. (See "Production of Liquids from Biomass by Continuous Fast Pyrolysis" in *Bioenergy* 84 *vol.* 3, *Biomass Conversion;* D. S. Scott, and J. Piskorz the contents of which are incorporated herein by reference).

A third method is a fast pyrolysis process which uses hot particulate solids and/or inert gases to rapidly transfer heat to the carbonaceous feedstocks in a reactor system (Rapid Thermal Processing). This results in very high gas or liquid yields from biomass depending upon the reactor conditions. Char yields are from 0 to 6% depending upon the feedstock, reactor temperature and residence time. Maximum gas yields are 90% of the feed stock mass at 900° C. and maximum liquid yields are 85% of the feed stock mass at 600°-650° C. This apparatus can be operated between 350° C. and 1000° C. with residence times between 0.030 seconds to 3.0 seconds.

Each of these fast pyrolysis methods offer much improved yields an improved quality of the liquid product and gaseous products where applicable, over conventional pyrolysis systems.

BRIEF DESCRIPTION OF THE DRAWINGS

Details of embodiments of the invention are described by reference to the accompanying drawings in which:

FIG. 4 is a graph of product yield by mass percent as a function of residence time in milliseconds.

FIG. 5 is a graph of yield of hydroxyacetaldehyde as a function of reactor temperature.

FIG. 6 is a graph of hydroxyacetaldehyde yield as a function of residence time at different temperatures.

DETAILED DESCRIPTION OF PREFERRED EMBODIMENTS

In the following descriptions the corresponding elements as shown in each figure of the drawings are given the same reference number.

While in the accompanying drawings and description, reference is made to the Rapid Thermal Processing, similar products can be achieved using the vacuum and flash pyrolysis systems as well as other systems that result in a high temperature with a limited residence time.

Figure 1:
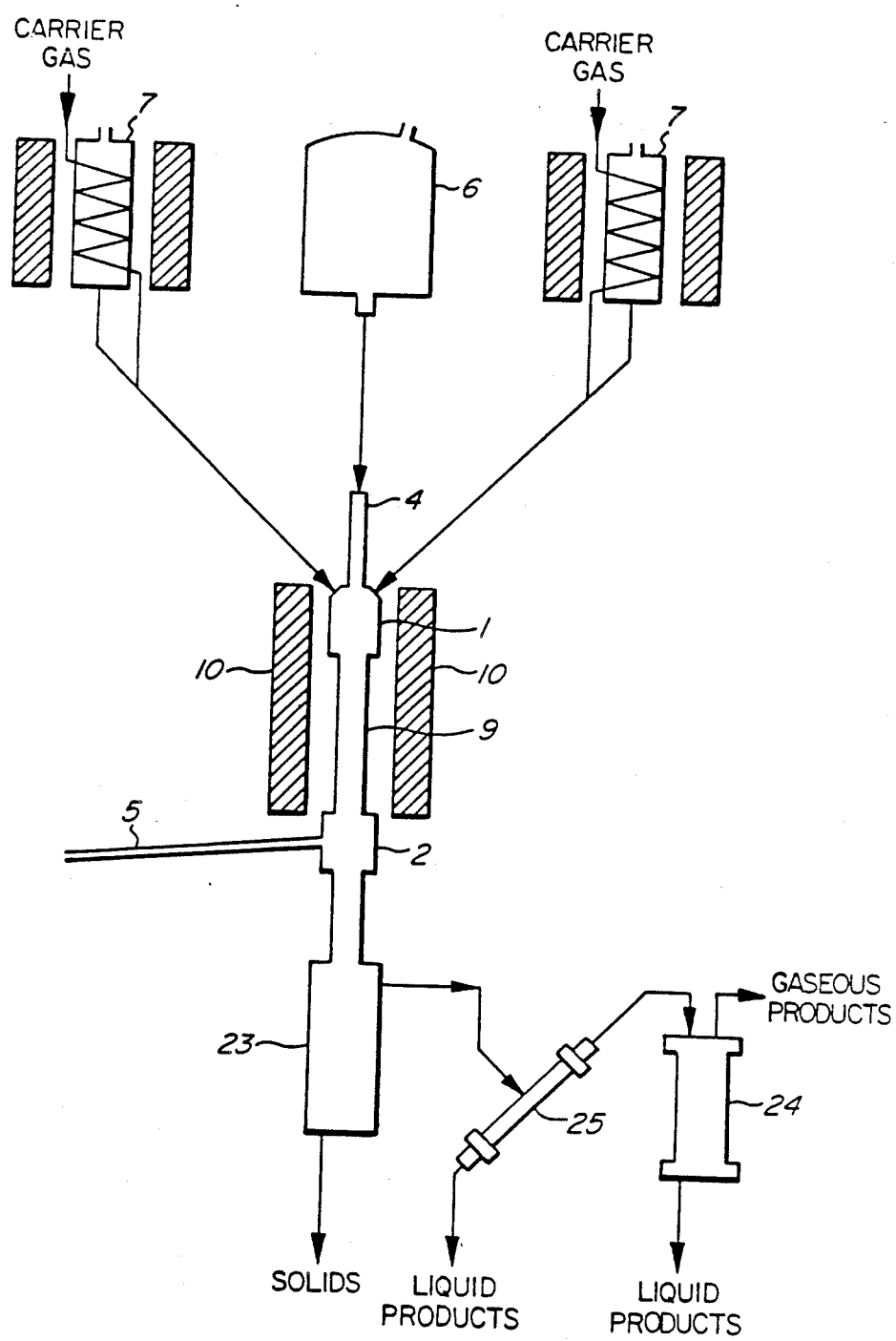
FIG. 1 is a schematic representation of one fast pyrolysis flow system known as rapid thermal processing.

The major components of the rapid thermal process are illustrated in FIG. 1. Rapid mixing and heat transfer are carried out in two vessels. The first vessel (1) the thermal mixer allows heat to be transferred to the wood from hot particulate solids or inert gas which can consist of gaseous nitrogen, suspended particulate solids, or a combination of the two. The second vessel (2), the quencher, allows fast quenching of the products to reduce secondary reactions of the initial pyrolysis products.

Figure 2:
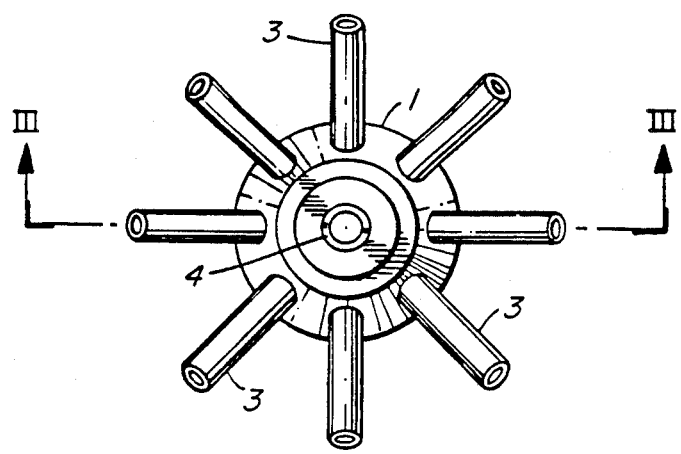
FIG. 2 is a top plan view of the reactor of the pyrolysis apparatus of FIG. 1.
Figure 3:
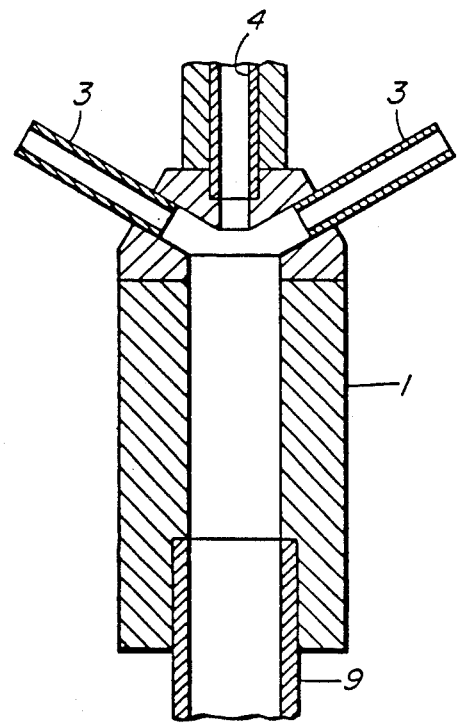
FIG. 3 is a section on the line III—III of FIG. 2.

As shown in FIGS. 2 and 3 the thermal mixer (1) has opposing converging inlets (3) for the solid heat carrier. This system effectively destroys the radial momentum of the heat carrier causing severe turbulence. Powdered wood feedstocks are then injected from the top of the thermal mixer (1) through a cooled tube (4) into the turbulent region where mixing occurs within 30 milliseconds.

After heating and mixing occurs, the wood or cellulose and the primary pyrolysis vapours are maintained at the reaction temperature for between 0.03 and 2.0 seconds depending upon the desired products. The primary pyrolysis vapours are produced as soon as the wood or cellulose is sufficiently heated to start the pyrolysis reactions.

The hot gaseous product is rapidly cooled (i.e. less than 30 milliseconds) by the injection of a single tangential stream of cryogenic nitrogen (5). Mechanical table feeders are used to supply wood to the reactor system. The solids pass from sealed hoppers (6) (which have a sufficient inventory of wood or particulate solids) through a double funnel system and are thereby metered onto a rotating table. Two fixed armatures sit near the surface of the rotating table and plough the solids off the outer circumference. From the table, the solids then fall into a conical chamber where they are picked up and carried into the transport line by nitrogen carrier gas. The overall range of the feed rate of biomass or particulate solids is controlled by setting the gap between the lower funnel and the table. Fine control is exercised by the rotation speed of the table.

When particulate solids are required to supply the process heat, the feeders (7) send hot particulate solids through a non-mechanical high temperature valve which operates at the reaction temperature. These hot solids are then sent on to the thermal mixer (1).

The solid particulate carbonaceous feedstock (or atomized carbonaceous liquids) is then injected axially into the reactor (1) through a water or air cooled tube (4) into the turbulent region where effective mixing and rapid heating to at least 400° C. occurs within 0.10 seconds, and preferably within 0.03 seconds.

The fast pyrolysis of wood is initiated in the thermal mixer (1) and continues in a transport reactor (9). The transport reactor is a length of pipe which is housed in an electrical oven (10). The mixture of hot gases and biomass passes from the thermal mixer (1), through the transport reactor (9), to the quencher (2) and to the solids separator (23). With the manipulation of the reactor volume and by manipulating heat carrier/biomass flow-rates, the residence time can be varied between 30 ms and 3.0 seconds. Reactor temperatures can be set in the range of 400° to 1000° C. Preferable reactor temperatures are between 400° to 800° C. and more preferably between 500° to 600° C. The heating rate that can be achieved with this apparatus is over 10,000° C. per second.

An efficient cyclonic condensor (25) is used to increase the yield of recovered liquid products. In addition an electrostatic precipitator (24) can be integrated into a downstream gas line to recover additional liquid products.

The wood feedstock can be any suitable wood product, but is preferably red maple. The feedstock should be ground to a fine 100 to 500 μm powder and then dried prior to use as the pyrolysis feedstock.

After collection of the condensates, water is added to cause phase separation to reduce benzo(a)pyrene, and tars. The amount of water added beyond that necessary to achieve effective phase separation is a matter of choice. The more water added, the greater the precipitation of higher molecular weight components. Water can be added beyond the phase separation to any desired degree to achieve a desired browning index level.

In application to wieners, solutions with browning indexes down to about 3 are useful in producing a desirable, smoke flavored and colored product. In some markets where browner, heavily smoked products are preferred, solutions of aqueous smoke flavorings with browning indexes of at least 20 are routinely used.

Where atomization is the preferred method of application, it is sometimes difficult to obtain sufficient smoke coloration on meats. In these situations smoke flavoring solutions with browning indexes ranging up to 30 are of use. The amount of water added to the condensates of the instant invention to produce a solution suitable for application to meats or other foods is a function of the effect sought by the processor.

Commercially available liquid smoke has browning indexes ranging from a 3 browning index minimum with a practical upper limit of about 30. This upper limit is a result of the limitations of prior methods of producing lquid smoke. The prior methods generally collect the water soluble condensation in a water bath and it is desired to keep the browning index below 13 to reduce the benzo(a)pyrene concentration. A browning index of above 13 is then achieved by concentration. In the result it becomes increasingly difficult and expensive to produce the liquid smoke above a browning index of 13. The difficulty and expense of concentration sets a practical upper limit of 30 as opposed to a limit beyond which solutions are not useful. On the contrary, if solutions were readily available with browning indexes of 30 or more they would be of particular use in atomization or as a starting material for application to casings as in U.S. Pat. No. 4,504,501. By adding little or no water to condensates of the instant invention, very high browning index sxolutions can be produced without need or expense of further concentration.

EXAMPLE 1

A general summary of the results of fast pyrolysis conducted using rapid thermal process apparatus between 650° and 800° C. using red maple feedstock and nitrogen as the heat carrier using the rapid thermal apparatus is given in Table 3. The apparatus used for these results was rated at 300 g of feedstock per hour. The yields for char and gas represent direct measurements and those for the liquids are by difference. These liquid yield values, however, are very close to the actual liquid yields as verified by the mass balance closures. All mass percent yields in Table 3 are expressed on a bone dry feedstock basis. It is clear from the results, that the char yields are significantly lower, and the liquid yields are significantly higher than the corresponding yields from conventional slow pyrolysis processes.

TABLE 3

SUMMARY OF THE RED MAPLE PYROLYSIS MASS BALANCE EXPERIMENTS

| Run number | Temp (C.) | Res Time (ms) | Gas Yield (%) | Condenser Liquids (%) | Remaining Liquids (%) | Char (%) | Total Recovery (%) |
|---|---|---|---|---|---|---|---|
| RA-21 | 650 | 234 | 24.18 | — | 70.52 | 5.97 | 100.67 |
| RA-22 | 650 | 217 | 22.87 | — | 67.89 | 5.96 | 96.72 |
| RA-24 | 650 | 392 | 23.69 | 22.18 | 42.00 | 7.79 | 95.67 |
| RA-25 | 650 | 194 | 19.83 | 19.69 | 45.75 | 9.69 | 94.96 |
| RA-26 | 650 | 1052 | 33.47 | 31.34 | 27.51 | 6.61 | 98.92 |
| RA-1 | 700 | 110 | 29.18 | 16.91 | 45.65 | 3.50 | 95.24 |
| RA-2 | 700 | 152 | 31.95 | 17.03 | 38.74 | 3.93 | 91.65 |
| RA-3 | 700 | 241 | 35.64 | 15.18 | 43.01 | 4.18 | 98.01 |
| RA-5 | 700 | 338 | 40.87 | 12.87 | 41.32 | 2.64 | 97.71 |
| RA-6 | 700 | 339 | 43.60 | 18.05 | 32.2 | 2.62 | 96.48 |
| RA-7 | 700 | 151 | 39.56 | 16.47 | 40.29 | 2.29 | 98.62 |
| RA-8 | 700 | 69 | 25.62 | 19.89 | 48.32 | 4.21 | 98.04 |
| RA-9 | 700 | 226 | 30.98 | 16.10 | 44.39 | 4.79 | 96.30 |
| RA-19 | 700 | 68 | 21.79 | — | 72.11 | 1.42 | 95.32 |
| RA-27 | 700 | 718 | 43.73 | 19.73 | 28.91 | 3.88 | 96.24 |
| RA-10 | 750 | 351 | 53.88 | 13.76 | 15.48 | 3.75 | 86.88 |
| RA-11 | 750 | 150 | 43.25 | 14.25 | 39.38 | 3.00 | 99.88 |
| RA-12 | 750 | 74 | 39.29 | 17.85 | 36.92 | 2.75 | 96.81 |
| RA-13 | 750 | 71 | 39.55 | 13.84 | 40.20 | 2.16 | 95.75 |
| RA-14 | 750 | 153 | 43.14 | 15.07 | 33.98 | 3.11 | 95.17 |
| RA-15 | 750 | 348 | 54.02 | 19.0 | 19.36 | 4.30 | 96.68 |
| RA-16 | 800 | 329 | 58.22 | 9.80 | 31.59 | 4.03 | 103.6 |
| RA-17 | 800 | 160 | 56.06 | — | 37.17 | 3.72 | 96.95 |
| RA-18 | 800 | 76 | 41.81 | — | 52.19 | 1.68 | 95.69 |

*Note:
— Where condenser liquids are not shown (value not recorded), remaining liquids represents entire liquid sample - These results are on an "as fed" basis.

EXAMPLE 2

Rapid Thermal Process Apparatus Operation and Results

Operating Parameters

Experiments were conducted using poplar wood ground to about 300 um (microns).

Wood moisture was about 1% (wet basis).

Wood was fed at a rate in the range of 3 to 5 kg/h.

Reaction temperatures were in the range of 400° to 650° C.

Vapor residence times were typically in the range of 600 to 1200 milliseconds (ms).

The heat carrier consisted of Ottawa silica sand with a mean particle size of about 150 microns and transported by inert nitrogen gas.

Equipment and Operating Procedure:

Rapid thermal processing apparatus of the type shown in FIGS. 1, 2 and 3, using hot particulate sand as the heat source was employed to produce liquid smoke. The apparatus is nominally rated at 5 kilograms of feedstock per hour. Three heat carrier feeders are used to heat up the sand heat carrier and deliver it to the transport lines. Each feeder is about 1.2 meters long and 150 mm outside diameter, and can hold 30 kg silica sand. The maximum feed rate is about 60 kg per hour (for each feeder) and the maximum temperature of the heat carrier is 1100° C. Feeder control is accomplished via a sparger tube and non-mechanical, high temperature "J" valve.

The poplar wood is air dried, milled and classified to a mean particle size of about 300 um. It is then oven dried prior to loading into the biomass feeder. The biomass feeder has an inventory of about 4 kg. Feed rates can be varied from 0 to about 10 kg per hour, and are independent of the transport gas flow rate and the solid carrier flow rate.

The wood feed material is delivered from the "biomass feeder" to the top of the reactor where it is injected into the cloud of turbulent hot solids. Extremely rapid heating of the feed material is achieved as the feedstock and hot sand particles are quickly and thoroughly mixed. After the fast, intimate mixing is complete, the feedstock and solid heat carrier pass through a tubular transport react whose length is adjusted to control the processing residence time. The reactor system consists of a rapid thermal mixer and two lengths of transport reactor. Each of these components is housed in its own oven with independent temperature control. Rapid mixing of the feedstocks with the solid heat carrier (i.e. sand) placed in the rapid thermal mixer is effected, and chemical reactions are then allowed to proceed in the transport reactor sections. The first reactor is 1.2 m in length while the second is 0.6 m. The reactor system components are constructed of Sch 40 Inconel 601 (40 mm I.D./1.5" nominal).

The products are rapidly cooled in the transfer line after the hot solids (char/sand) are removed in a solids "catch pot" or drop-out vessel. Additional cooling is carried out in the primary (water-cooled) and secondary (dry ice/acetone-cooled) condensers, where condensation of vapours and recovery of liquids also occur. The solids catch pot is an inertial separator constructed of stainless steel which can hold about 100 kg of hot solids. Separation of the gases from the solids is based on the lower momentum of the gas/vapour product (compared to the hot sand) which can change direction more readily than the solids, and escape into the transfer line to be quenched directly with nitrogen gas.

The primary condenser is a water-jacketed carbon steel pipe (having both an inner and outer water-jacket) which is lined with a chemical resistant paint. The cooling water enters at about 19° C. and cools the product to about 35° C.

The secondary condenser is also a lined, carbon-steel pipe which is not jacketed but sits directly in an insulated acetone/dry ice bath. It has a tangential gas/vapour inlet which forces the products to the condenser wall where efficient heat transfer can occur. The secondary unit yields a gas exit temperature of about −5° C.

Parallel filters are used to collect persistent aerosols, and the clean gas is then directed through an orifice meter to quantify the flow for mass balance closure. A fractional quantity of the product gas is continuously "bled" from the main stream to a gas sample bag for subsequent analyses. The three parallel filters are contructed of stainless steel, have a pore size of 0.5 microns and are housed in a single filter vessel. Each of these units are about 50 mm in diameter (outside) and about 0.5 mm long.

After a run, the condenser, filters and transport lines are washed with acetone, the solution is filtered, and the acetone is evaporated under vacuum to yield the liquid product. Char is determined by ashing several representative samples of the char/sand mixture which is recovered from the solids separator. Gases are analyzed by standard gas chromatography techniques.

TABLE 4

SUMMARY OF POPLAR WOOD PYROLYSIS MASS BALANCE EXPERIMENTS

| RUN NUMBER | TEMP. (°C.) | RES. TIME (ms) | PRODUCT YIELDS (% of wood feed) | | |
|---|---|---|---|---|---|
| | | | Gas | Liquid | Char |
| 9 | 660 | 800 | 32.9 | 60.3 | 6.8 |
| 10 | 525 | 835 | 14.9 | 78.0 | 7.0 |
| 11 | 465 | 1215 | 7.0 | 86.0 | 7.0 |
| 12 | 590 | 960 | 20.5 | 71.8 | 7.7 |

EXAMPLE 3

Fluidized Bed Operation and Results

Fluidized Bed Operation

Operating Parameters:

Experiments were conducted using poplar wood ground to −595 microns (−30 mesh).

Wood moisture was about 6% (wet basis).

Wood was fed at a rate of 1 to 2.5 kg/h.

Reaction temperatures (in the bed) were in the range of 400° to 650° C.

Vapor residence times were typically in the range of 500 to 700 milliseconds (ms).

The fluidized bed consisted of Ottawa silica sand with a mean particle size of about 720 microns.

Recycled product gas (primarily CO, $CO_2$ and $CH_4$) was used to fluidize the sand and to transport the wood feedstock into the reactor.

Equipment and Operating Procedure:

Poplar wood (or other wood species, straw or peat) is air dried, milled and screened to −595 um particle size.

The prepared wood is conveyed from a hopper into a variable speed twin-screw feeder and discharged into a flow of recycled product gas. It is then conveyed into the fluidized bed reactor directly into the fluidized bed region.

The reactor bed consisted of highly spherical Ottawa silica sand with a mean particle size of about 720 um.

The fluidizing gas (primarily CO, $CO_2$ and $CH_4$) is preheated in the inlet line by electrical heaters and enters the bed through a porous stainless steel plate at a rate which is equivalent to 1.2 to 2 times the minimum fluidization velocity.

The reactor is wrapped with heating coils for supplemental heating.

Pyrolysis products and the recycle gases are swept from the top of the reactor into a cyclone where the dry char is removed from the gas/vapor phase. The gases and vapors are then passed to two condensers and on to a series of filters.

The first condenser is normally operated at 20° C. while the second is maintained at about 0° C.

The filter train consists of an in-line 5 um (micron) mesh screen followed by a filter vessel packed with glass wool.

After a run, the condensers are washed with acetone, the solution is filtered, and the acetone is evaporated under vacuum to yield the liquid product. The filters are weighed before and after an experiment and the contents are recovered if the quantity is significant.

Char is collected in the char pot (at the cyclone exit) and weighed.

Gases are analyzed by standard gas chromatography techniques.

TABLE 5

FLUIDIZED BED RESULTS: RAPID PYROLYSIS OF POPLAR WOOD

| TEMP. (°C.) | RES. TIME (ms) | PRODUCT YIELDS (% of wood feed) | | | TOTAL RECOVERY % |
|---|---|---|---|---|---|
| | | Gas | Liquid + | Char | |
| 425 | 616 | 6.0 | 59.6 (55.9) | 30.5 | 96 |
| 450 | 689 | 8.6 | 61.1 (55.8) | 25.5 | 95 |
| 465 | 584 | 8.6 | 72.7 (67.2) | 18.9 | 100 |
| 500 | 550 | 12.5 | 75.1 (65.8) | 12.2 | 100 |
| 500 | 550 | 12.1 | 77.8 (71.2) | 11.2 | 101 |
| 500 | 600 | 11.9 | 70.1 (65.8) | 13.2 | 95 |
| 541 | 539 | 21.2 | 71.1 (63.7) | 9.0 | 101 |
| 541 | 539 | 19.1 | 69.8 (62.1) | 9.7 | 99 |
| 550 | 555 | 18.6 | 67.3 (62.0) | 10.6 | 96 |
| 625 | 520 | 36.7 | 44.4 (40.3) | 7.8 | 99 |

+ The values in parentheses are total organic liquids (ie. moisture-free) The difference is moisture (water) in the liquid sample. - Similar experiments have been conducted with maple and spruce with similar overall yields of char, gas and liquid.

As is apparent from the data in Tables 3, 4 and 5, the preferred operating temperature is at the lower ranges with a relatively short residence time of 300–600 milliseconds. However good yields are achieved throughout the operating range of the rapid thermal processing equipment and over a variety of residence times. As shown in FIG. 4 the shorter the residence time that can be achieved, the higher the yields of the preferred liquid product.

As noted above, the yield of hydroxyacetaldehyde is a good indication of the browning ability of the liquid smoke. Yields of this compound versus reactor temperature and residence time are set out in FIGS. 5 and 6. FIG. 5 is a graph of hydroxyacetaldehyde yields of the fast pyrolysis of wood against temperature.

FIG. 5 confirms that the optimum reaction temperatures are between 500° and 600° C. FIG. 6 also confirms that the optimum conditions are between 500° and 600° C. with a short residence time.

EXAMPLE 4

A sample of the fluidized bed reactor liquid pyrolysate referred to in Example 3 was diluted with water according to the following proportions. The water soluble fraction was separated and analyzed.

TABLE 6

DILUTIONS OF FAST PYROLYSIS LIQUIDS

| weight % fast pyrolysis liquids in total solution | Acids % w/w | Phenols % w/w | Carbonyls % w/w | Browning Index Units | Specific Gravity @ 21° C. | Benzo(a) pyrene ppb |
|---|---|---|---|---|---|---|
| 100 | 10.5 | 5.50 | 32.5 | 49.0 | 1.245 | 19.0 |
| 85 | 9.1 | 3.75 | 29.2 | 46.8 | 1.201 | 14.0 |
| 80 | 8.7 | 3.31 | 26.6 | 45.6 | 1.182 | 3.6 |
| 70 | 7.9 | 2.42 | 21.4 | 35.8 | 1.148 | 0.5 |
| 65 | 7.5 | 2.10 | 20.2 | 33.8 | 1.120 | 0.5 |
| 60 | 6.5 | 1.65 | 17.5 | 31.5 | 1.112 | 0.5 |
| 40 | 4.1 | 0.820 | 10.3 | 18.2 | 1.065 | 0.5 |
| 20 | 2.8 | 0.430 | 5.4 | 12.2 | 1.028 | 0.5 |
| 10 | 1.3 | 0.230 | 4.9 | 5.6 | 1.011 | 0.5 |

These results are indicative of the advantage to adding sufficient water to cause enough phase separation to reduce the B(a)P content to less than 0.5 ppb. As can be seen from Tables 7 and 8 the resulting solutions have substantially higher carbonyl to phenol and browning index to phenol ratios than commercially available solutions produced by slow pyrolysis processes.

TABLE 7

RATIO OF CARBONYL AND BROWNING INDEX TO PHENOLS

| Weight % of fast pyrolysis liquids in total solution | Browning index | Carbonyls/ phenols | Browning index/ phenols |
|---|---|---|---|
| 100 | 49.0 | 5.90 | 8.91 |
| 85 | 46.8 | 7.79 | 12.5 |
| 80 | 45.6 | 8.04 | 13.8 |
| 70 | 35.8 | 8.84 | 14.8 |
| 65 | 33.8 | 9.62 | 16.1 |
| 60 | 31.5 | 10.6 | 19.1 |
| 40 | 18.2 | 12.6 | 22.2 |

TABLE 8

AVERAGE OF TEN REPRESENTATIVE RATIOS FROM SLOW PYROLYSIS LIQUID SMOKE SOLUTIONS

| Acid Concentration % w/w | Browning index | Carbonyls/ phenols | Browning index/ phenols |
|---|---|---|---|
| 11.5 | 9.8 | 6.47 | 5.76 |
| 6.2 | 5.3 | 7.78 | 6.17 |

As seen in both tables 7 and 8 the ratios are higher in more dilute solutions. This is because the solubility of carbonyls is the same regardless of concentration while phenols are less soluble in more dilute solutions. Thus, the advantage of water addition to fast pyrolysis serves two purposes, to reduce phenols thereby reducing flavor while maintaining a high browning potential, and to reduce benzo(a)pyrene solubility to less than 0.5 ppb.

As can be seen by comparing Tables 7 and 8 at an equivalent browning index, the ratios of carbonyls to phenols and browning index to phenols is significantly greater with fast pyrolysis liquids than with conventional liquid smoke. The higher ratio with fast pyrolysis liquids results in a darker product at a given flavor level. This permits coloring of food with a less smoky flavor or alternatively to achieve a darker product at comparable flavor intensities.

The lowest browning index used for smoking meat is about 3.0. This browning index would be used for direct application to foodstuffs. Based on the above results the fast pyrolysis product could be diluted to about a 6.1% w/w solution and still have a browning index above 3.0.

EXAMPLE 5

Results of the Application of Fast Pyrolysis Liquids to Wieners

1. Color/Browning Test Panel

About 2.5 lb. strands of skinless wieners obtained from Cher-Make Sausage Co. (Manitowoc, WI) were dipped for 60 seconds in the following:
A. Water (control)
B. A 10% (W/W) Solution of Fast Pyrolysis Liquids (Fluidized Bed)

The wieners were cooked to an internal temperature of 70° C. according to the following schedule:
43.3° C. for 10 minutes
60.0° C. for 45 minutes
71.1° C. for 25 minutes
82.2° C. until the internal temp. was 70° C.

After cooking, the wieners were placed in a 4.4° C. cooler overnight for subsequent evaluation and testing.

The following day, the wieners were peeled and a panel of 9 observers were asked to indicate which set had the most appealing brown color. All 9 indicated that sample B was noticeably browner than the water dipped control (and therefore more appealing).

The results are indicative of the ability of the aqueous solutions of fast pyrolysis liquids to react with meat surfaces to give a desirable smoked appearance.

2. Taste Comparison Test Panel

About 2.5 lb strands of skinless wieners obtained from Cher-Make Sausage Co. (Manitowoc, WI) were dipped for 60 seconds in the following:
A. A 10% (W/W) Solution of Fast Pyrolysis Liquids (Fluidized Bed)
B. A solution of slow pyrolysis liquid smoke made according to Hollenbeck, U.S. Pat. No. 3,106,473, the Browning Index of which was 3.9.

The wieners were cooked to an internal temperature of 70° C. according to the following schedule:
43.3° C. for 10 minutes
60.0° C. for 45 minutes
71.1° C. for 25 minutes
82.2° until the internal temp. was 70° C.

The following day, a panel of 9 were asked to asked to taste the wieners which had been peeled and warmed to 49° C. A triangular method (i.e. using 3 samples, two of the same treatment and one of the other) was used to determine whether the panelists could distinguish between the two treatments.

The results indicated that only one of the 9 panel members could determine a difference between aqueous solutions of fast pyrolysis liquids and conventional smoke flavorings when applied to the wieners. This is not statistically significant and the usefulness of the former for smoking meats is indicated.

The procedures for determining phenol and carbonyl content in liquid smoke are as follows:
Determination of Phenol and Carbonyl Content of Liquid Smoke For sample preparation, all samples are filtered through Whatman No. 2 filter paper or equivalent, and refrigerated upon receipt or after preparation until the time of analysis to avoid possible polymerization. Distilled water is used for all dilutions. The samples are diluted with water in two steps, beginning with a 10 ml. quantity. In the first step the dilution is to a total volume of 200 ml., and in the second step 10 ml. of the first solution is further diluted to a total volume of 100 ml. For phenol determination, 5 ml. of the second solution is further diluted in a third step with distilled water to a total volume of 100 ml. For carbonyl determination, 1 ml. of the second solution is further diluted with carbonyl-free methanol to a total volume of 10 ml.

For the phenol determination, the reagents are:
1. Boric acid-potassium chloride buffer pH 8.3:
Dilute the indicated quantities of the solution to 1 liter with water.
0.4M Boric Acid-125 ml.
0.4M Potassium chloride-125 ml.
0.2M Sodium hydroxide-40 ml.
2. 0.6% NaOH
3. Color reagent: 2,6-dichloroquinonechlormide.
Stock solution: Dissolve 0.25 mg. in 30 ml. methanol and keep in refrigerator.
4. 2,6-Dimethoxyphenol (DMP) standards: Prepare solutions of 1 to 7 micrograms/ml. of DMP in water for standard curve.

This procedure for phenol determination is a modified Gibbs method based on the procedure described in Tucker, I. W. "Estimation of Phenols in Meat and Fat", JAOAC, XXV, 779 (1942). The reagents are mixed together in the following order:
1st-5 ml. of pH 8.3 buffer.
2nd-5 ml. of dilution of unknown diluted liquid smoke, or of standard 2,6-dimethoxyphenol solution, or 5 ml. of water for blank.
3rd-Adjust pH to 9.8 using 1 ml. of 0.6% NaOH.
4th-Dilute 1 ml. of color reagent stock solution to 15 ml. in water. Add 1 ml. of diluted color reagent. Prepared just before adding.
5th-Allow color to develop for exactly 25 minutes at room temperature.
6th-Determine absorbance at a wave length of 580 nm in a 1 cm colorimeter tube with a Spectronic 20 or equivalent.
7th-Prepared a standard curve using absorbance as the abscissa and standard concentrations as the ordinate. Extrapolate concentration of DMP in liquid smoke dilutions from this curve.
8th-Calculate mg DMP/ml liquid smoke using the following equation:

$$\frac{\text{ppm DMP (from std. curve)} \times \text{(dilution factor)} \times 0.001 \text{ mg/g}}{\text{ml of original liquid smoke sample}} = \frac{\text{mg DMP/ml}}{\text{liquid smoke}}$$

To calculate mg DMP/g liquid smoke, divide result of above equation by the weight (g) of 1 ml. of liquid smoke.

For carbonyl determination, the reagents are:

1. Carbonyl-free methanol: To 500 ml. of methanol add 5 gm. of 2,4-dinitrophenylhydrazine and a few drops of concentrated HCl. Reflux three hours, then distill.

2. 2,4-Dinitrophenylhydrazine solution: Prepare saturated solution in carbonyl-free methanol using twice recrystallized product. Store in refrigerator and prepare fresh every two weeks.

3. KOH solution: Add 10 gm. of KOH solid to 20 ml. of distilled $H_2O$ and dilute to 100 ml. with carbonyl-free methanol.

4. 2-Butanone standard: Prepare solutions of 3.0 to 10 mg. of 2-butanone in 100 ml. carbonyl-free methanol for a standard curve.

The procedure is a modified Lappan-Clark method based on the procedure described in their article "Colorimetric Method for Determination of Traces of Carbonyl Compounds", Anal. Chem. 23, 541–542 (1959).

The procedure is as follows:

1st-To 25 ml. volumetric flasks containing 1 ml. of 2,4-dinitrophenylhydrazine reagent (prewarmed to insure saturation) add 1 ml. of diluted liquid smoke solution, or 1 ml. of standard butanone solution, or 1 ml. of methanol (for reagent blank).

2nd-Add 0.05 ml. of concentrated HCl to all 25 ml. flasks, mix contents of each, and place in water bath for 30 minutes at 50° C.

3rd-Cool to room temperature and add 5 ml. KOH solution to each.

4th-Dilute contents of each flask to 25 ml. with carbonyl-free methanol.

5th-Read at 480 nm against methanol blank set at absorbance of 0, (cuvettes-0.5×4 in (10.2 cm) or equivalent). Use Spectronic 20, or equivalent.

6th-Plot absorbance versus 2-Butanone (MEK) concentration in mg. per 100 ml. for standard curve.

7th-Prepare a standard curve using absorbance as the abscissa and standard concentrations (mg MEK/100 ml.) as the ordinate. Extrapolate concentration of MEK in liquid smoke dilutions from this curve.

8th-Calculate mg MEK/100 ml. liquid smoke by the following equation:

$$\frac{\text{mg MEK (from std curve)} \times \text{(dilution factor)}}{100 \text{ ml}} = \frac{\text{mg MEK/100}}{\text{ml liq smoke}}$$

To calculate mg MEK/g liquid smoke, divide the result of the above equation by the weight (in grams) of 100 ml. of smoke.

The procedures for determining the browning index are as follows:

Determination of Browning Index of Liquid Smoke

The browning index is a relative measure of the ability of carbonyls to react with the amino acid glycine. Tests have shown good correlation between the browning index values of a solution of smoke flavoring and the extent of brown color formation in meat surface. The test does not employ a standard curve as do some colorimetric analyses, but a standard is run to ensure accuracy. The reaction is carried out in dilute aqueous buffered solution. For each sample two test tubes are prepared, one with and one without glycine. The latter is necessary to account for the background color of the solution. The difference between the optical densities @ 400 nm is multiplied by the dilution factor to obtain the browning index in BIU/ml.

Reagents:

0.5M NaOH: Dilute 10 g to 500 ml in a volumetric flask.

0.1M potassium hydrogen phthalate buffer: to a two liter volumetric flask add 20.42 g potassium hydrogen phthalate and 152 ml 5.M NaOH. Dilute to volume. Check pH to ensure it is 5.5.

Glycine buffer: add 2 g glycine to a 200 ml volumetric flask and dilute to volume with phthalate buffer. Store below 10° C.

Glyoxal standard: add 0.5 ml of 40% glyoxal solution to a 50 ml volumetric flask. Dilute to volume with distilled water. React 1 ml of the standard solution according to the procedure below. The optical density should read 0.300. If not, adjust the concentration as necessary. Store below 10 C.

Procedure:

One pair of 20×150 mm test tubes is used for each sample.

Pipette 10 ml of the phthalate buffer into one tube and 10 ml of glycine phthalate buffer into the other. Cap the tubes with marbles and temper the tubes in a boiling water bath for 5 min.

Add 1 ml of the appropriately diluted solution to both tubes (the concentration in the dilution should be between 0.2 and 0.4 BIU/ml). Add 1 ml of distilled water to a tube containing 10 ml glycine buffer (reagent blank). Add 1 ml of glyoxal standard to a tube containing 10 ml glycine buffer (standard).

Allow the reaction to proceed at 100° C. for exactly 10 min., remove the tubes from the bath and place them in an ice bath for 2 min. Transfer the solutions to ½ inch cuvettes. Use the glycine-water solution blank to set the spectrophotometer to zero optical density @ 400 nm. Determine the optical density of both the reacted and unreacted samples and the standard.

Calculations: The optical density of the unreacted control is substrated from that of the reacted sample to obtain the net increase in the optical density due to the yellow-orange color formed by the browning reaction. If the O.D. of the glyoxal standard is other than 0.300, correct the reacted sample O.D. values by adding one half of the difference between the 0.300 and the value obtained to the O.D. difference obtained from the samples Multiply by the dilution factor to obtain the browning index units/ml.

Even though only the Rapid Thermal Processing apparatus was described herein, the invention defined by the following claims is intended to cover any use of the products of a fast pyrolysis method as liquid smoke flavoring.

The embodiments of the invention in which an exclusive property or privilege is claimed are defined as follows:

1. A process of making an aqueous wood smoke flavored solution for use in foodstuffs comprising:
   (1) heating in the absence of oxygen ground wood or cellulose to between 400° C. and 650° C. within 1.0 second;
   (2) maintaining the said wood or cellulose together with the pyrolysis products produced from the said wood or cellulose between 400° C. and 650° C. for between 0.03 and 2.0 seconds;
   (3) reducing the temperature of the pyrolysis products to below 350° C. within 0.6 seconds thereby obtaining a liquid extract;

(4) separating and collecting the liquid extract of the said pyrolysis products;

(5) diluting the said liquid extract with water to achieve a partial phase separation and to obtain an aqueous wood smoke flavored solution having a benzo(a)pyrene concentration of less than 1.0 ppb and a browning index to phenol concentration greater than 8.9 to 1 and a ratio of hydroxyacetaldehyde to acetol greater than 5.5 to 1.

2. The process according to claim 1 in which the wood or cellulose and the pyrolysis are maintained between 400° C. and 650° C. for between 0.03 and 0.60 seconds.

3. The process according to claim 1 or 2 in which the benzo(a)pyrene concentration is reduced to less than 0.5 ppb.

4. The process according to claim 3 in which the process is carried out in rapid thermal processing apparatus.

5. The process according to claim 3 in which the process is carried out in a fluidized bed reactor.

6. The process of flavoring and coloring an edible food which comprises:

(1) heating ground wood or cellulose in the absence of oxygen to at least 400° C. within 1.0 second;

(2) maintaining the said wood or cellulose together with the pyrolysis products produced from the said wood or cellulose at a temperature of at least 400° C. for between 0.03 and 0.6 seconds;

(3) reducing within 0.6 seconds the temperature of the said pyrolysis products to at least 300° C. thereby obtaining a liquid extract;

(4) separating and collecting the liquid extract of the said pyrolysis products;

(5) diluting the said liquid extract with water to achieve a partial phase separation and to obtain an aqueous wood smoke flavored solution having a benzo(a)pyrene concentration of less than 1.0 ppb and a browning index to phenol concentration greater than 8.9 to 1 and a ratio of hydroxyacetaldehyde to acetol greater than 5.5 to 1; and (6) contacting the food with the resulting aqueous smoke flavored solution.

7. The process according to claim 6 in which the benzo(a)pyrene concentration is reduced to less than 0.5 ppb.

8. The process of imparting a wood smoke flavor to an edible food which comprises:

(1) heating in the absence of oxygen ground wood or cellulose to at least 400° C. within 1.0 seconds;

(2) maintaining the said wood or cellulose together with the pyrolysis products produced from the said wood or cellulose at a temperature of at least 400° C. for between 0.03 and 0.60 seconds;

(3) reducing the temperature of the pyrolysis products thereby obtaining a liquid extract;

(4) separating and collecting the liquid extract of the said pyrolysis products; and (5) diluting the said liquid extract with water to achieve a partial phase separation and to obtain an aqueous wood smoke flavored solution having a benzo(a)pyrene concentration of less than 0.5 ppb. and a browning index to phenol concentration greater than 8.9 to 1 and a ratio of hydroxyacetaldehyde to acetol greater than 5.5 to 1; and (6) contacting the food with the resulting aqueous smoke flavored solution.

9. A process of making an aqueous wood smoke flavored solution for use in foodstuffs comprising:

(1) heating in the absence of oxygen wood or cellulose to between 400° C. to 650° C. within 1.0 second;

(2) maintaining the said wood or cellulose together with the pyrolysis products produced from the said wood or cellulose between 400° C. and 650° C. between 0.03 and 2.0 seconds;

(3) reducing the temperature of the pyrolysis products to below 350° C. within 0.6 seconds thereby obtaining a liquid extract;

(4) separating and collecting the liquid extract of the said pyrolysis products;

(5) diluting the said liquid extract with water to achieve a partial phase separation and to obtain an aqueous wood smoke flavored solution having a benzo(a)pyrene concentration of less than 1.0 ppb and a browning index to phenol concentration greater than 8.9 to 1 and a ratio of hydroxyacetaldehyde to acetol greater than 5.5 to 1.

10. The process according to claim 9 in which the benzo(a)pyrene concentration is reduced to less than 0.5 ppb.

11. The process according to claim 10 in which the process is carried out in a vacuum pyrolysis reactor.

12. A process of imparting a wood smoke flavor to an edible food comprising:

(1) collecting the liquid condensate produced by fast or flash pyrolysis of ground wood or cellulose in the absence of oxygen, without the addition of water over a time period of between about 0.6 to 2.6 seconds;

(2) combining one part of the said liquid condensate with 0.25 to 25 parts by weight of water to achieve partial phase separation and then separating the resulting non-aqueous phase from the aqueous phase constituting the desired liquid smoke solution to obtain an liquid smoke solution having a benzo(a)pyrene concentration of less than 1.0 ppb and a browning index to phenol concentration greater than 8.9 to 1 and a ratio of hydroxyacetaldehyde to acetol greater than 5.5 to 1;

(3) applying the liquid smoke solution to a foodstuff.

13. The process according to claim 12 in which one part of the pyrolysis liquid condensate is combined with between 0.30 to 20 parts by weight of water and then separating the resulting non-aqueous phase from the aqueous phase constituting the desired liquid smoke solution.

14. A process according to claim 12 in which sufficient water is added to produce a liquid smoke solution containing no more than 0.5 ppb of benzo(a)pyrene.

15. A process of browning and imparting a smoke flavor to a meat product comprising:

(i) contacting a meat product with an aqueous liquid solution containing up to 10 percent by weight of products from the fast pyrolysis of wood or cellulose products having a benzo(a)pyrene concentration of less than 1.0 ppb and a browning index to phenol concentration greater than 8.9 to 1 and a ratio of hydroxyacetaldehyde to acetol greater than 5.5 to 1, the products from the fast pyrolysis formed by:

(1) heating in the absence of oxygen ground wood or cellulose to at least 400° C. within 1.0 second;

(2) maintaining said wood or cellulose together with the gas and vapor pyrolysis products produced from said wood or cellulose at a temperature of at least 400° C. for between 0.03 and 0.60 seconds;

(3) reducing the temperature of the gas and vapor pyrolysis products to below 300° C. within 0.60 seconds thereby obtaining a liquid extract;

(4) extracting said liquid extract with water to form a water soluble liquid extract;

(5) separating and collecting the water soluble liquid extract of said pyrolysis products thereby obtaining the aqueous liquid solution; and (ii) cooking said meat product to an internal temperature of at least 70° C.

16. A process according to claim 15 wherein said meat product is a meat product contained within a casing.

17. A process according to claim 16 wherein said meat product is a weiner.

* * * * *